United States Patent [19]

Okayama et al.

[11] Patent Number: 4,747,297
[45] Date of Patent: May 31, 1988

[54] APPARATUS FOR ANALYZING PARTICULATES

[75] Inventors: Junji Okayama; Naoki Noguchi; Hiroyuki Amimoto, all of Kyoto, Japan

[73] Assignee: Horiba, Ltd., Kyoto, Japan

[21] Appl. No.: 12,650

[22] Filed: Feb. 9, 1987

[30] Foreign Application Priority Data

Feb. 10, 1986 [JP] Japan .................................. 61-27082

[51] Int. Cl.$^4$ ........................................... G01N 15/06
[52] U.S. Cl. ....................................................... 73/28
[58] Field of Search ..................................... 73/28, 23

[56] References Cited

U.S. PATENT DOCUMENTS

| | | | |
|---|---|---|---|
| 3,986,386 | 10/1976 | Beltzer et al. | 73/28 |
| 4,257,258 | 3/1981 | Bovenlander | 73/23 |
| 4,567,750 | 2/1986 | Artmann | 73/28 |
| 4,586,367 | 5/1986 | Lewis | 73/28 X |
| 4,633,706 | 1/1987 | Ito et al. | 73/28 |
| 4,660,408 | 4/1987 | Lewis | 73/28 |

Primary Examiner—Stewart J. Levy
Assistant Examiner—Joseph W. Roskos
Attorney, Agent, or Firm—Wenderoth, Lind & Ponack

[57] ABSTRACT

An apparatus for measuring and analyzing the concentration or weight of particulates in the exhaust gas from a diesel engine. The apparatus includes a carbon particle detector which continuously measures dry soot concentration and high and low temperature HC detectors which respectively continuously measure the concentrations of gaseous hydrocarbon compounds (1) in a high-temperature undiluted state immediately upon leaving the diesel engine and (2) in a low-temperature diluted and cooled state after dilution with room air. Standard gas detectors are provided for both the high-temperature undiluted exhaust gas and the diluted and cooled exhaust gas in order to continuously determine the amount of dilution of the diluted exhaust gas. Outputs from the detectors are input to a computer to provide continuous determination of the total concentration or weight of particulates which are composed of soot particles and soluble organic fractions, as well as separate determinations of these components.

4 Claims, 1 Drawing Sheet

APPARATUS FOR ANALYZING PARTICULATES

BACKGROUND OF THE INVENTION

1. Field of the Invention

The present invention relates to an apparatus for measuring and analyzing a concentration or a weight of particulates included in an exhaust gas from a diesel engine, in particular a high-temperature exhaust gas exhausted from a diesel engine and then diluted and cooled with air having a room temperature.

2. Description of the Prior Art

It has been known that particulates included in low-temperature exhaust gas consist of DS (dry soot), which is a substance insoluble in organic solvents (for example dichlormethane), and SOF (soluble organic fractions), which is a substance soluble in organic solvents. Of these substances, the former, that is to say DS, is mainly formed of agglomerated spherical carbon particles having a crystalline structure and generally observed as a black smoke since they are turned black in color, while the latter, that is to say SOF, consists of drops of condensed hydrocarbon and lubricating oil as a preceding-stage substance of soot and generally observed as a white smoke or a blue smoke since it turns white or blue in color after being exhausted.

That is to say, carbon particles and gaseous hydrocarbon compounds (including high boiling point hydrocarbon compounds and low boiling point hydrocarbon compounds) are contained in a high-temperature exhaust gas immediately after being exhausted from a diesel engine. Upon diluting and cooling this high-temperature exhaust gas exhausted from the diesel engine with air having a room temperature, the high boiling point hydrocarbon compounds are condensed to turn into fine liquid drops, thereby forming the SOF, which generates the particulates together with DS generated from said carbon particles.

Accordingly, the concentration or the weight of high boiling point hydrocarbon compounds in the high-temperature exhaust gas immediately after being exhausted from the diesel engine always shows a high correlation with the concentration or weight of the SOF. In addition, particulates consisting of DS and SOF and the low boiling point hydrocarbon compounds, which remain in the gaseous form, are contained in a low-temperature exhaust gas exhausted from the diesel engine and then diluted and cooled with air having a room temperature.

However, since the particulate exhaust characteristics, in short the concentrations or the weights of DS and SOF constituting said particulates, are remarkably varied in dependence upon the operating conditions such as load, rotation speed and the like of the engine, it is important for the attainment of fundamental data indicative of an improvement in the particulate exhaust characteristics of the engine to not only determine a total concentration or a total weight of particulates exhausted, but also individually determine the concentration or the weight of DS and SOF.

Previously, measurements and analyses of these particulates have been carried out by using the following filter-weighing method:

An exhaust gas from a diesel engine is filtered to sample particulates (DS and SOF) contained in the exhaust gas onto a filter, and then the sample is subjected to a particulate extraction treatment to dissolve SOF in organic solvents (for example dichlormethane) and leave DS on the filter, and then the weight of the remainder (SOF) left after heating and vaporizing said organic solvents is measured by means of a balance. The weight of the substance (DS) trapped on said filter insoluble in the organic solvents is also measured by means of the balance.

However, the above described conventional method takes a very long time for the measurement and the analysis to be completed since it usually takes about 8 hours for the extraction of SOF. This method also has the disadvantages of requiring a remarkably complicated manual measuring and analyzing procedure, and only an intermittent measurement and analysis can be carried out.

SUMMARY OF THE INVENTION

The present invention was achieved in view of the above and it is an object of the present invention to provide an apparatus for analyzing particulates, capable of continuously and automatically measuring and analyzing not only a total concentration or a total weight of particulates contained in an exhaust gas exhausted from a diesel engine, but also the individual concentrations or weights of carbon particles (DS) and soluble organic fractions (SOF), which are constituent elements of said particulates, in a remarkably short time with only minimal manual operation.

An apparatus for analyzing particulates according to the present invention is adapted to automatically calculate and output not only a total concentration or weight of particulates generated when an exhaust gas exhausted from a diesel engine is diluted and cooled, but also individual concentrations or weights of its constituents, that is of carbon particles (DS), and high boiling point hydrocarbon compounds which have a high correlation with the soluble organic fractions (SOF). This known correlation is hereinafter called the "SOF-correlative factor". The apparatus continuously measures the concentration of carbon particles (DS) by means of a carbon particle detector, continuously measures the total concentration of gaseous hydrocarbon compounds in a high-temperature exhaust gas immediately after being exhausted from the diesel engine by means of a high-temperature HC detector and continuously measures a remaining concentration of the gaseous hydrocarbon compounds left in a low-temperature exhaust gas which has been automatically diluted and cooled, by means of a low-temperature HC detector. The amount of dilution in the diluted exhaust gas is determined from continuous measurements of the concentration of a standard gas in the high-temperature exhaust gas made by means of a high-temperature standard gas detector and continuous measurements of the concentration of the standard gas in the diluted low-temperature exhaust gas made by means of a low-temperature standard gas detector, so that the measurement and analysis of particulates can be made automatically and continuously within a remarkably short time without requiring complicated manual operations such as a particulate extraction treatment as in the conventional apparatus.

DETAILED DESCRIPTION OF THE PREFERRED EMBODIMENT

Figure 1:
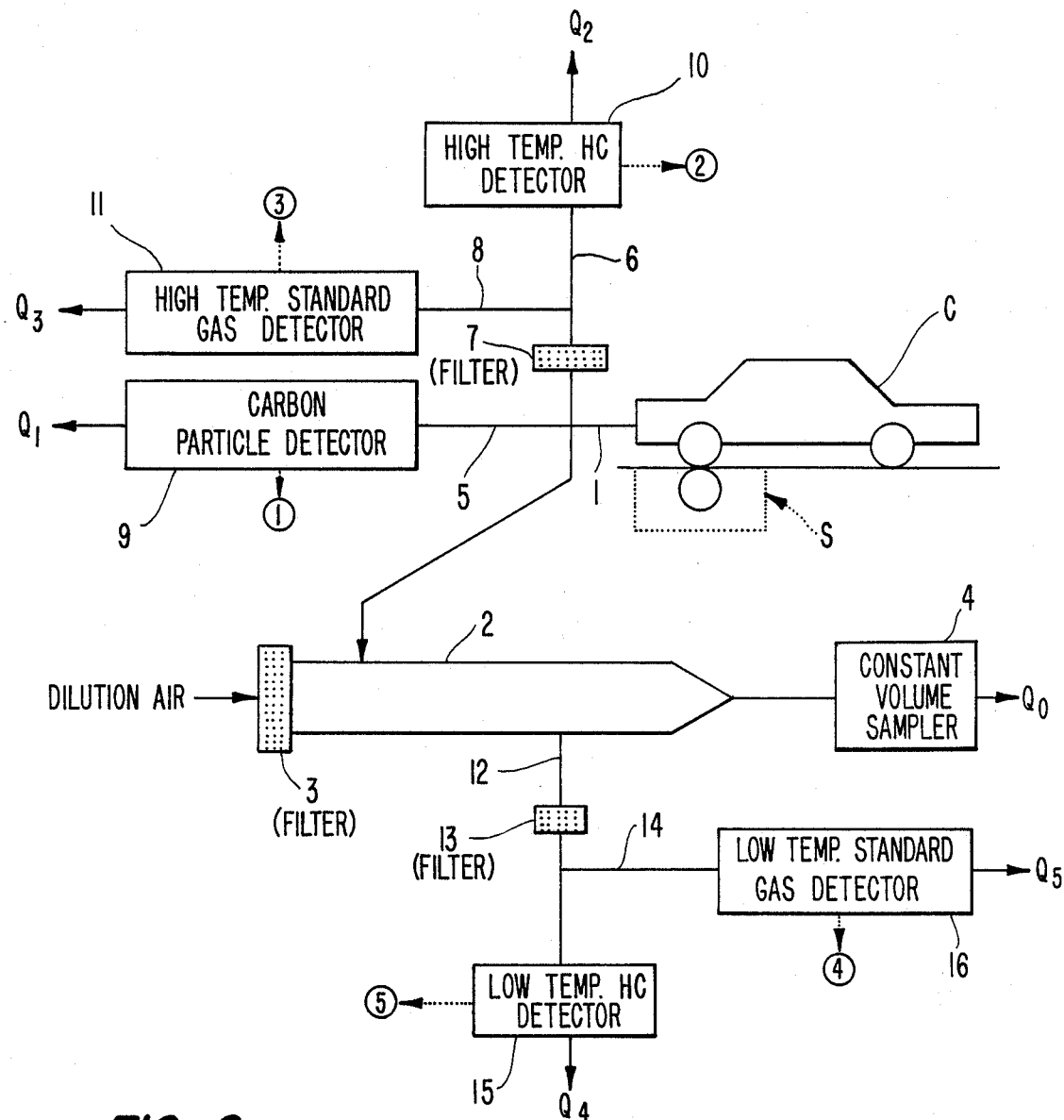
FIG. 1 is a block diagram showing one preferred embodiment of the testing and measuring parts of an apparatus for analyzing particulates according to the present invention.

A preferred embodiment of an apparatus for analyzing particulates according to the present invention will be below described with reference to the drawing.

Referring now to the drawing, as shown in FIG. 1, reference C designates a motor vehicle provided with a diesel engine (not shown) which is disposed to simulate operating conditions on a real road by means of a chassis dynamometer S such as is disclosed in U.S. Pat. No. 4,327,578.

Almost all high-temperature exhaust gas exhausted from the diesel engine of the motor vehicle C is introduced through a main exhaust pipe 1 into an upstream end of a dilution tunnel 2 where the high-temperature exhaust gas is diluted and cooled with room temperature dilution air introduced through a filter 3. In addition, the dilution tunnel 2 is provided with a CVS (Constant Volume Sampler) 4 such as is disclosed in U.S. Pat. No. 3,699,814, connected thereto at a downstream part thereof for drawing and discharging the diluted exhaust gas at a constant flow rate $Q_0$ so that a diluted exhaust gas well pass through the dilution tunnel 2 always at a constant flow rate.

The main exhaust pipe 1 is provided with a first branch exhaust pipe 5 and a second branched exhaust pipe 6 for separately diverting a very small portion of the high-temperature exhaust gas exhausted from the diesel engine at a place very close to the motor vehicle, the second branch exhaust pipe 6 being provided with a filter 7 for removing carbon particles (DS) and other foreign matter in the exhaust gas. A third branch exhaust pipe 8 extends from a downstream end of the filter 7. The first, second and third branch exhaust pipes 5, 6 and 8 are sufficiently short and/or thermally insulated or further heated, if necessary, so as to prevent any substantial cooling of the high-temperature exhaust gas in the pipes immediately after being exhausted from the diesel engine.

The first branch exhaust pipe 5 is provided with a carbon particle detector 9 capable of continuously measuring the concentration of carbon particles (DS) in the high-temperature exhaust gas exhausted from said diesel engine. An EDM (Electron Diffusibility Measurement) detector is used as the carbon particle detector 9. This EDM detector is adapted to continuously measure the concentration by weight of carbon particles (DS) by measuring the electric conductivity of the exhaust gas, taking advantage of the fact that the electric conductivity of the carbon particles (DS) is substantially higher than that of the soluble organic fractions (SOF). In the apparatus, the flow rate of the high-temperature exhaust gas flowing through said carbon particle detector 9 is set at a very small constant value $Q_1$.

The second branch exhaust pipe 6 is provided with a high-temperature HC detector 10 capable of continuously measuring the total concentration by volume of gaseous hydrocarbon compounds (high boiling point hydrocarbon compounds and low-boiling point hydrocarbon compounds) in the high-temperature exhaust gas immediately after being exhausted from the diesel engine. A so-called FID (Flame Ionization Detector) is used as the high-temperature HC detector 10. The flow rate of the high-temperature exhaust gas flowing through said high-temperature HD detector 10 is set at a very small constant value $Q_2$.

The third branch exhaust pipe 8 is provided with a high-temperature standard gas detector 11 capable of continuously measuring a concentration of a standard gas normally found in diesel exhaust gases (for example $CO_2$ gas, $NO_x$ gas or the like), in the high-temperature exhaust gas. A non-dispersion type infrared analyzer is used as this high-temperature standard gas detector. The flow rate of the high-temperature exhaust gas flowing through the high-temperature standard gas detector 11 is set at a very small constant value $Q_3$.

The dilution tunnel 2 is provided with a first branch pipe 12 for drawing off a very small amount of the low-temperature exhaust gas diluted and cooled in the dilution tunnel 2, connected to a downstream part thereof, the first branch pipe 12 being provided with a filter 13 for removing high boiling point hydrocarbon compounds liquefied by the cooling, carbon particles (DS) and other foreign matter in the exhaust gas, and a second branched pipe 14 is connected to the downstream end thereof.

The first branch pipe 12 is provided with a low-temperature HC detector 15 capable of continuously measuring the concentration by volume of gaseous hydrocarbon compounds (only low boiling point hydrocarbon compounds) which remain in the diluted low-temperature exhaust gas at the downstream end of the second branch pipe 12. A FID is also used as this low-temperature HC detector 15. The flow rate of the low-temperature exhaust gas flowing through this low-temperature HC detector 15 is set at a very small constant value $Q_4$.

The second branch pipe 14 is provided with a low-temperature standard gas detector 16 capable of continuously measuring the concentration of the standard gas (gas of the same kind as the above described) in the low-temperature exhaust gas. A non-dispersion type infrared analyzer is also used as this low-temperature standard gas detector 16. The flow rate of the low-temperature exhaust gas passing through this low-temperature standard gas detector 16 is set at a very small constant value $Q_5$.

The amount of dilution of the exhaust gas in the dilution tunnel 2 is determined by a comparison of the concentration value detected by the low-temperature standard gas detector 16 with the concentration value detected by the high-temperature standard gas detector 11, as will be described in greater detail below.

The concentration by volume of only high boiling point hydrocarbon compounds showing a high correlation with soluble organic fractions (SOF) is determined from the determined amount of dilution in dilution tunnel 2, the concentration value detected by the high-temperature HC detector 10 and the concentration value detected by the low-temperature HC detector 15.

Figure 2:
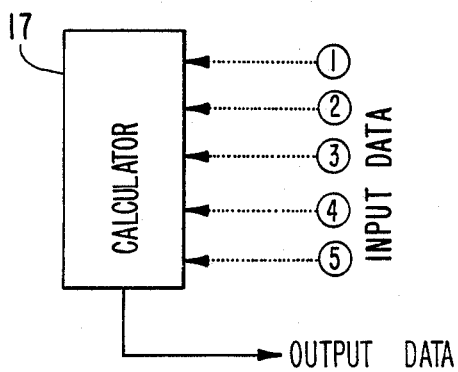
FIG. 2 is a diagram of the calculating part of the apparatus according to the invention.

As shown by a dotted arrow and marks ①, ②, ③, ④, ⑤, in FIG. 1 of the drawing, all of the detected value data (measured results) output from the detectors 9, 10, 11, 15, 16 is input to the calculating means 17 (e.g. electronic computer) 17 shown in FIG. 2.

The calculating means 17 continuously and automatically calculates and outputs data indicating the total concentration of particulates generaed when the exhaust gas exhausted from the diesel engine is diluted and cooled, the individual concentration by weight of only the carbon particles (DS) in the exhaust gas and the individual concentration by weight of high boiling hydrocarbon compounds showing a high correlation with soluble organic fractions (SOF), in the exhaust gas, by the following equations, respectively:

(I) The individual concentration by weight of carbon particles (DS) in the dilution tunnel 2 = (the concentration value detected by the carbon particle detector 9) × (the concentration value detected by the low-temperature standard gas detector 16)/(the concentration value detected by the high-temperature standard gas detector 11), wherein the ratio: (the concentration value detected by the low-temperature standard gas detector 16)/(the concentration value detected by the high-temperature standard gas detector 11) (hereinafter "the dilution factor") expresses the amount of dilution of the exhaust gas with room temperature air in the dilution tunnel 2.

(II) The individual concentration by weight of high boiling point hydrocarbon compounds (SOF-correlative substances) in the dilution tunnel 2 = [(the concentration value detected by the high-temperature HD detector 10) × (the concentration value detected by the low-temperature standard gas detector 16)/(the concentration value detected by the high-temperature standard gas detector 11) − (the concentration value detected by the low-temperature HC detector 15)] × (a scale factor correlating the concentration by volume to a concentration by weight).

(III) The total concentration by weight of particulates in the dilution tunnel 2 = [the computed value of the individual concentration by weight of DS by the above described equation (I)] + [(the computed value of the individual concentration by weight of high boiling point hydrocarbon compounds by the above described equation (II)] × (the SOF-correlative factor).

In addition, if the flow rate $Q_o$ through the CVS 4 is also input to or preset in the computer 17 to multiply it by the results (concentrations by weight) calculated by the above described equations (I), (II), (III), not only the total weight of particulates generated when the exhaust gas exhausted from the diesel engine is diluted and cooled but also the rough value of the individual weight of the carbon particles (DS) and soluble organic fractions (SOF) constituting the particulates can be calculated. If the flow rates $Q_1$, $Q_2$, $Q_3$, $Q_4$, $Q_5$ of the sample drawn through the detectors 9, 10, 11, 15, 16 are input to the computer 17 and a precise total flow rate $Q = (Q_1 + Q_2 + Q_3) + (Q_o + Q_4 + Q_5) \times$ (the dilution factor) of the exhausted gas exhausted from the diesel engine is used in place of the flow rate $Q_o$, the total weight of particulates and the individual weights of each constituent element can be even more accurately calculated.

The carbon particle detector 9 is supplied with the high-temperature exhaust gas immediately after being exhausted from the diesel engine in the above described preferred embodiment because of the possibility that the EDM detector of the carbon particle detector 9 may be influenced by the soluble organic fractions (SOF) if allowed to cool in the case where their concentration is great. However, in a case where the concentration of the soluble organic fractions (SOF) is known to be sufficiently small that their influence can be disregarded, the carbon particle detector 9 may be arranged at the downstream end of the dilution tunnel 2 to supply it with the low-temperature exhaust gas which has been diluted and cooled.

As is obvious from the above detailed description, an apparatus for analyzing particulates according to the present invention is provided with a carbon particle detector, a high-temperature HC detector, a low-temperature HC detector, a high-temperature standard gas detector and a low-temperature standard gas detector having the above described functions, as well as the calculating means for automatically calculating and outputting the total concentration or total weight of particulates, the individual concentration or weight of carbon particles (DS) and the individual concentration or weight of the high boiling point hydrocarbon compounds having a high correlation with the soluble organic fractions (SOF), on the basis of the values detected by the detectors. As a result, not only the total concentration or weight of particulates contained in the exhaust gas exhausted from the diesel engine, but also the individual concentrations or weights of the carbon particles (DS) and the soluble organic fractions (SOF) constituting the particulates in the exhaust gas can be automatically and continuously measured and analyzed within a remarkably short time without requiring the conventional troublesome manual operations such as particulate extraction which takes a long time, whereby the invention is capable of very efficiently and in detail investigating the transient particulate generating states under the varied operating conditions of the diesel engine, such as acceleration and deceleration. Thus, the invention can greatly contribute to various kinds of research and development.

What is claimed is:

1. An apparatus for analyzing particulates in the exhaust gas of a diesel engine, comprising:

carbon particle measuring means, including a carbon particle detector, for continuously measuring and outputting a first value indicative of the concentration of carbon particles in the exhaust gas;

first hydrocarbon measuring means, including a high-temperature hydrocarbon detector, for continuously measuring and outputting a second value indicative of the total concentration of gaseous hydrocarbon compounds including high and low boiling point gaseous hydrocarbon compounds, in a first portion of the exhaust gas while the first portion is at a high temperature immediately after being exhausted from the diesel engine;

means for diluting and cooling a second portion of the exhaust gas;

second hydrocarbon measuring means, including a low-temperature hydrocarbon detector, for continuously measuring and outputting a third value indicative of the total concentration of low boiling point gaseous hydrocarbon compounds in the second portion of the exhaust gas cooled and diluted by said diluting and cooling means;

first standard gas measuring means, including a high-temperature standard gas detector, for continuously measuring and outputting a fourth value indicative of the concentration of a standard gas found in diesel engine exhaust and which remains gaseous at room temperature, in the first portion of the exhaust gas;

second standard gas measuring means, including a low-temperature standard gas detector, for continuously measuring and outputting a fifth value indicative of the concentration of the standard gas in the second portion of the exhaust gas, the ratio of the fifth value to the fourth value being indicative of the amount of dilution of the exhaust gas by said diluting and cooling means;

calculating means, responsive to said first, second, third, fourth and fifth values, for automatically calculating and outputting at least one value from among the values of the total concentration and weight of particulates formed of carbon particles and soluble organic fractions in the exhaust gas, at least one value from among the values of the concentration and weight of the carbon particles, and in the exhaust gas, and at least one value from among the values of the concentration and weight of the high boiling point hydrocarbon compounds in the exhaust gas.

2. An apparatus as in claim 1, wherein said carbon particle measuring means, including said carbon particle detector, comprises means for measuring and outputting the first value indicative of the concentration of carbon particles in a third portion of the exhaust while the third portion is at a high temperature immediately after being exhausted from the diesel engine.

3. An apparatus as in claim 2, wherein the first, second and third portions are separate portions of the exhaust gas, said apparatus further comprising means for receiving the exhaust from the diesel engine and branching it into said first, second, and third portions of the exhaust gas and then directing said portions of the exhaust gas to said carbon particle measuring means, said first hydrocarbon measuring means and said second hydrocarbon measuring means.

4. An apparatus as in claim 1, wherein the first and second portions are separate portions of the exhaust gas, said apparatus further comprising means for receiving the exhaust from the diesel engine and branching it into said first and second portions and then directing said portions of the exhaust gas to said first and second hydrocarbon measuring means.

* * * * *